US00PP20493P2

(12) United States Plant Patent
Schräder

(10) Patent No.: US PP20,493 P2
(45) Date of Patent: Nov. 17, 2009

(54) **VARIETY OF *BIDENS* PLANT NAMED 'SUMBID 05'**

(50) Latin Name: *Bidens ferulifolium*
Varietal Denomination: Sumbid 05

(75) Inventor: Ralf Schräder, Lüdinghausen (DE)

(73) Assignee: Grünewald Veredelings B.V., 's Gravenzande (NL)

( * ) Notice: Subject to any disclaimer, the term of this patent is extended or adjusted under 35 U.S.C. 154(b) by 0 days.

(21) Appl. No.: 12/283,539

(22) Filed: Sep. 12, 2008

(51) Int. Cl.
*A01H 5/00* (2006.01)

(52) U.S. Cl. ..... Plt./410

(58) Field of Classification Search ..... Plt./410
See application file for complete search history.

*Primary Examiner*—Kent L Bell
(74) *Attorney, Agent, or Firm*—The Webb Law Firm

(57) ABSTRACT

A new and distinct *Bidens ferulifolium* plant named 'Sumbid 05 ' with a compact growth habit and bicolored yellow flowers.

2 Drawing Sheets

Botanical classification: *Bidens ferulifolium.*
Varietal denomination: 'Sumbid 05'.

BACKGROUND OF THE INVENTION

The present invention comprises a new and distinct cultivar of *Bidens ferulifolium* known by the varietal name 'Sumbid 05'. The new variety was discovered in 's Gravenzande, The Netherlands on Apr. 3, 2006. The new variety has been asexually reproduced via tip cuttings and the first date of asexual reproduction was Oct. 27, 2006 in 's Gravenzande, The Netherlands. The new variety is the result of a planned breeding program cross between unpatented *Bidens ferulifolium* plant 'Sumbid 02' (female parent) and unpatented *Bidens ferulifolium* plant No. M009-4. (male parent). The purpose of the breeding program was to develop new varieties that exhibit similar growth habits to the parent varieties, but with a broad range of color. The new variety exhibits a compact growth habit and 8 ray florets that are similar to characteristics of both parents, but differs from both parents and other *Bidens ferulifolium* varieties known to the breeder with its bicolored flowers. 'Sumbid 05' also exhibits early flowering like 'Sumbid 02' (commercially known as "Olympic Star"). The new variety has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
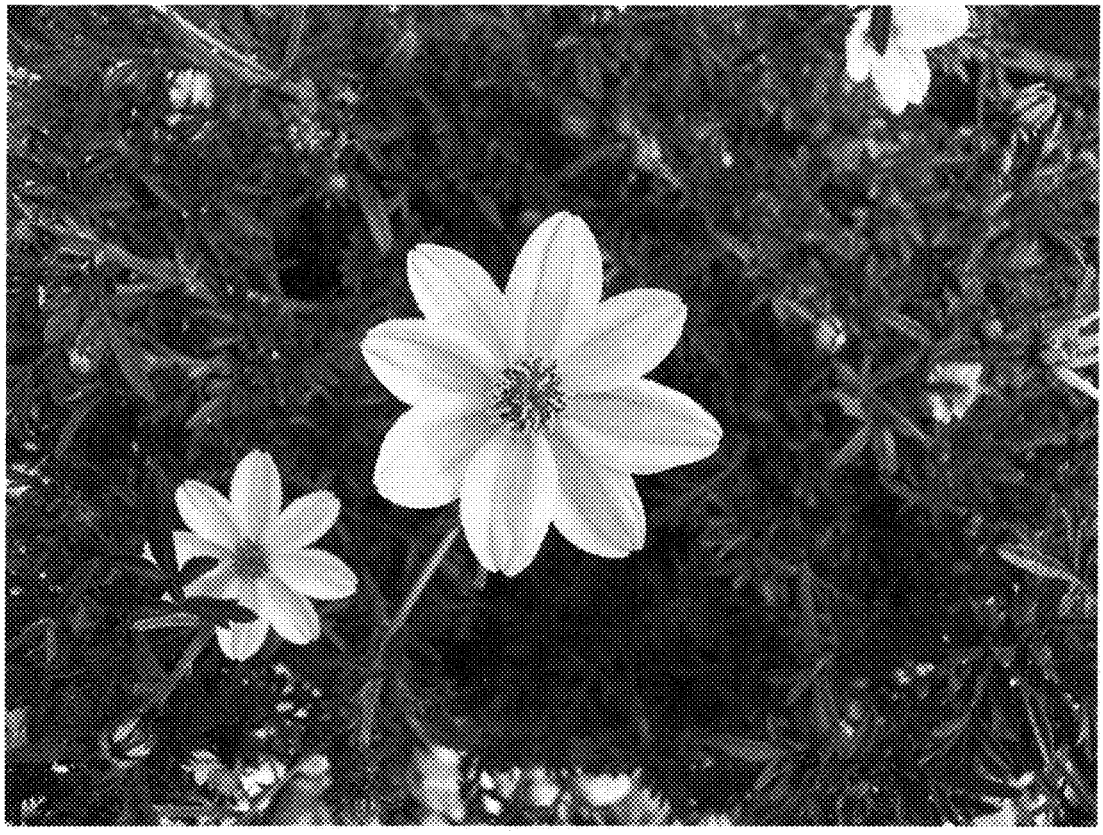
FIG. 1 is a close-up view of a view of the blossoms of the new variety.
Figure 2:
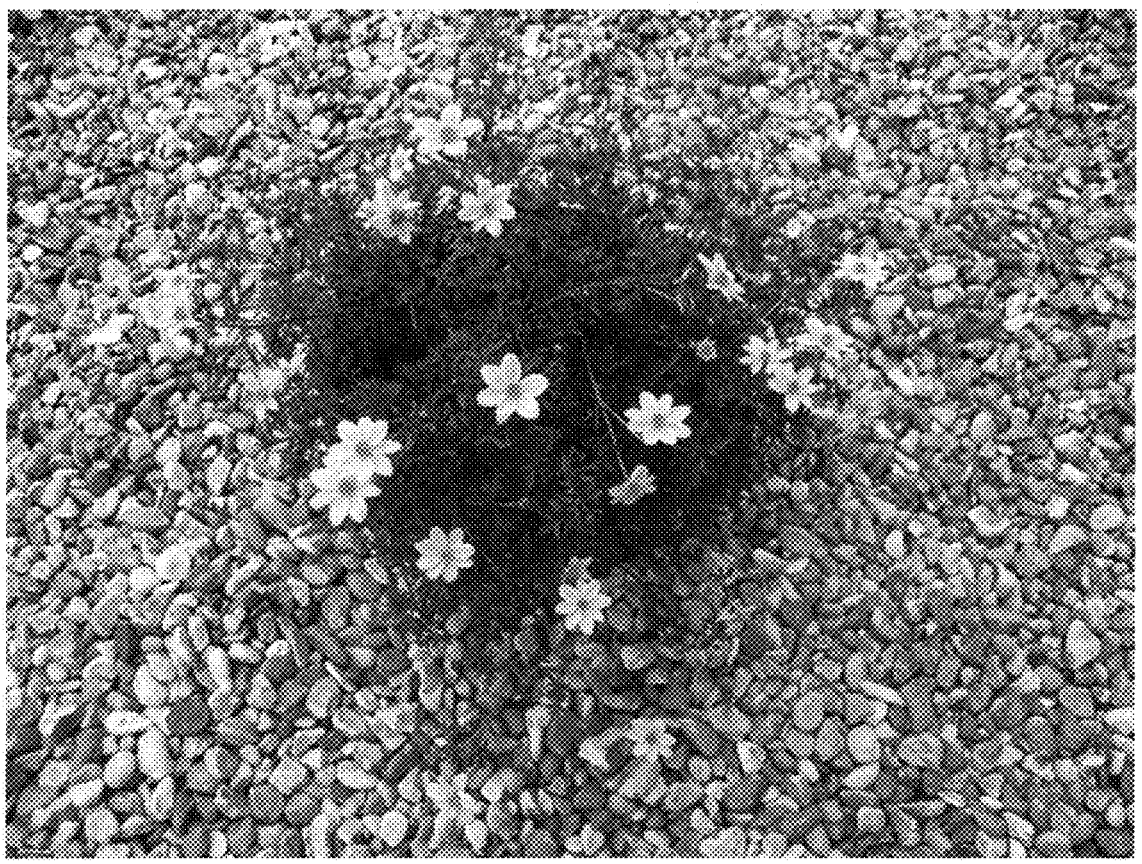
FIG. 2 is a view of an entire plant of the new variety.

The following detailed description sets forth the characteristics of a 3 month old 'Sumbid 05' plant grown outside in a 25 cm container having 15-10-10 NPK fertilizer at 1 promille per week in The Netherlands. The temperature was 10–14° C. at night and 20–28 ° C. during the day. The color readings were taken indoors under natural light. Color references are primarily to The R.H.S. Colour Chart of The Royal Horticultural Society of London.

PLANT

Time to initiate roots: About 10 days at about 18° C.
Time to develop roots: About 14 days at about 18° C.
Time to produce a finished flowering plant from a rooted cutting: About 10 weeks in a 12 cm container.
Root description: Fine, 161D.
Rooting habit: Strong and spreading.
Form: Spreading.
Height: 20–25 cm.
Plant diameter: 30–40 cm.
Vigor: Compact.
Branching habit: Spreading.
Lateral branches:
- *Length.*—Primary: 15–20 cm. Secondary: 4–6 cm.
- *Diameter.*—Primary: 2–3 mm. Secondary: 1–2 mm.
- *Internode length.*—12–18 mm.
- *Texture.*—Smooth.
- *Pubescence.*—Some very fine hairs are present.
- *Color.*—138 C.

Foliage:
- *Arrangement.*—Opposite.
- *Size of leaf.*—Length: 20–24 mm. Width: 20–22 mm.
- *Shape of leaf.*—Pinnate.
- *Shape of apex.*—Acuminate.
- *Shape of base.*—Round.
- *Texture.*—Upper surface: Smooth. Lower surface: Smooth.
- *Aspect.*—Smooth.
- *Margin type.*—Smooth.
- *Pubescence.*—Upper surface: Smooth. Lower surface: Smooth.
- *Color.*—Young leaves: Upper surface: 139A. Lower surface: 147B. Mature leaves: Upper surface: 139A. Lower surface: From 147B to 147C.
- *Petiole.*—Shape: Round. Length: Approximately 5–8 mm. Diameter: 1 mm. Color: From 147B to 147C.

*Veins.*—Venation type: Alternate. Color: Upper surface: 139A. Lower surface: 139C.

INFLORESCENCE

Buds (described 3 days before opening):
*Shape.*—Round.
*Diameter.*—7 mm.
*Length.*—10 mm.
*Color.*—1A.
Natural flowering season: From April to November in The Netherlands.
Appearance:
*Form.*—8 consistent ray florets like an aster.
Inflorescence position: Single at the end of the branches.
Disc and ray floret arrangement: Consistent.
Number of inflorescences per branch: 2–4.
Lasting quality: 5–6 days.
Fragrance: Mild.
Disease and/or pest resistance: None observed to date.
Temperature tolerance: 0° C.–40° C.
Drought tolerance: None observed.
Size:
*Diameter.*—35–40 mm.
*Height* (*depth*).—6–8 mm.
*Diameter of disc.*—7 mm.
Ray florets:
*Length.*—16–18 mm.
*Width.*—10 mm.
*Shape.*—Oval.
*Apex.*—Round; crenate once per floret.
*Base.*—Round.
*Margin.*—Smooth.
*Aspect.*—Thin and weak.
*Texture.*—Smooth.
*Number per inflorescence.*—8.
*Color.*—When opening: Upper surface: 9B. Lower surface: 9B. At maturity: Upper surface: 8B, with 9A inside. Lower surface: 7C. Upon fading: Upper surface: 8D, with from 9A to 9B inside. Lower surface: 7C to 7D.
Disc florets:
*Length.*—5–6 mm.
*Width.*—Less than 1 mm.
*Shape.*—Round.
*Number per inflorescence.*—Approximately 30.
*Color.*—At first opening: N144B. At maturity: 153C to 153D. Upon fading: 151A.
Phyllaries:
*Length.*—3 mm.
*Width.*—1 mm.
*Shape.*—Lanceolate.
*Apex.*—Acuminate.
*Margin.*—Entire.
*Number per inflorescence.*—8.
*Texture.*—Smooth.
*Color.*—Upper surface: 136A. Lower surface: 137B.
Peduncle:
*Length.*—25–35 mm.
*Diameter.*—1–1.5 mm.
*Aspect.*—Round.
*Texture.*—Smooth.
*Color.*—147B to 147C.

REPRODUCTIVE ORGANS

Androecium:
*Presence.*—No androecium to see.
Gynoecium:
*Presence.*—On disc florets.
*Pistils.*—Number: Approximately 36. Length: Approximately 3 mm. Style: Length: Approximately 1 mm. Color: 12A. Stigma: Shape: T-shaped, then tapered and closed. Color: 12A.
Seeds:
*Description of conditions when produced.*—Only in the hot, dry summer months.
*Color.*—N200A.
*Length.*—Approximately 4 mm.
*Width.*—Approximately 1 mm.
*Number.*—Approximately 10 per inflorescence.

I claim:

1. A new and distinct variety of *Bidens ferulifolium* plant named 'Sumbid 05' substantially as shown and described herein.

* * * * *